United States Patent

Kötzsch et al.

[11] 4,101,397
[45] Jul. 18, 1978

[54] PROCESS FOR THE PREPARATION OF ALPHA-CHLOROMETHYLSILANES

[75] Inventors: Hans-Joachim Kötzsch; Gerhard Müller, both of Rheinfelden; Hans-Joachim Vahlensieck, Wehr, all of Fed. Rep. of Germany

[73] Assignee: Dynamit Nobel Aktiengesellschaft, Troisdorf, Fed. Rep. of Germany

[21] Appl. No.: 783,372

[22] Filed: Mar. 31, 1977

[30] Foreign Application Priority Data

Apr. 2, 1976 [DE] Fed. Rep. of Germany ....... 2614197

[51] Int. Cl.² .............................................. B01J 1/10
[52] U.S. Cl. ..................... 204/158 HA; 260/448.2 E
[58] Field of Search ................................ 204/158 HA

[56] References Cited

U.S. PATENT DOCUMENTS

| | | | |
|---|---|---|---|
| 2,612,510 | 9/1952 | Hatcher et al. | 204/158 HA X |
| 3,840,447 | 10/1974 | Lücking et al. | 204/158 HA |
| 3,912,604 | 10/1975 | Lücking et al. | 204/158 HA |

*Primary Examiner*—Paul F. Shaver

*Attorney, Agent, or Firm*—Burgess, Dinklage & Sprung

[57] ABSTRACT

An improvement in a process for the preparation of an α-chloromethylsilane of the general formula $$ClCH_2(CH_3)_{3-n}SiCl_n (n = 0 \text{ to } 3) \quad \text{II}$$

by chlorination of a methylchlorosilane of the general formula $$(CH_3)_{4-n}SiCl_n \quad \text{I}$$

with elemental chlorine while exposing the reaction mixture to light, the improvement residing in maintaining the reaction mixture at a temperature in the vicinity of the boiling point of the methylsilane to be chlorinated by regulating the metering in of methylsilane to be chlorinated and continuously passing chlorine gas through the reaction zone at a constant rate and withdrawing reaction product at such a rate that the concentration of chloromethylsilane amounts up to 18 weight percent.

9 Claims, 1 Drawing Figure

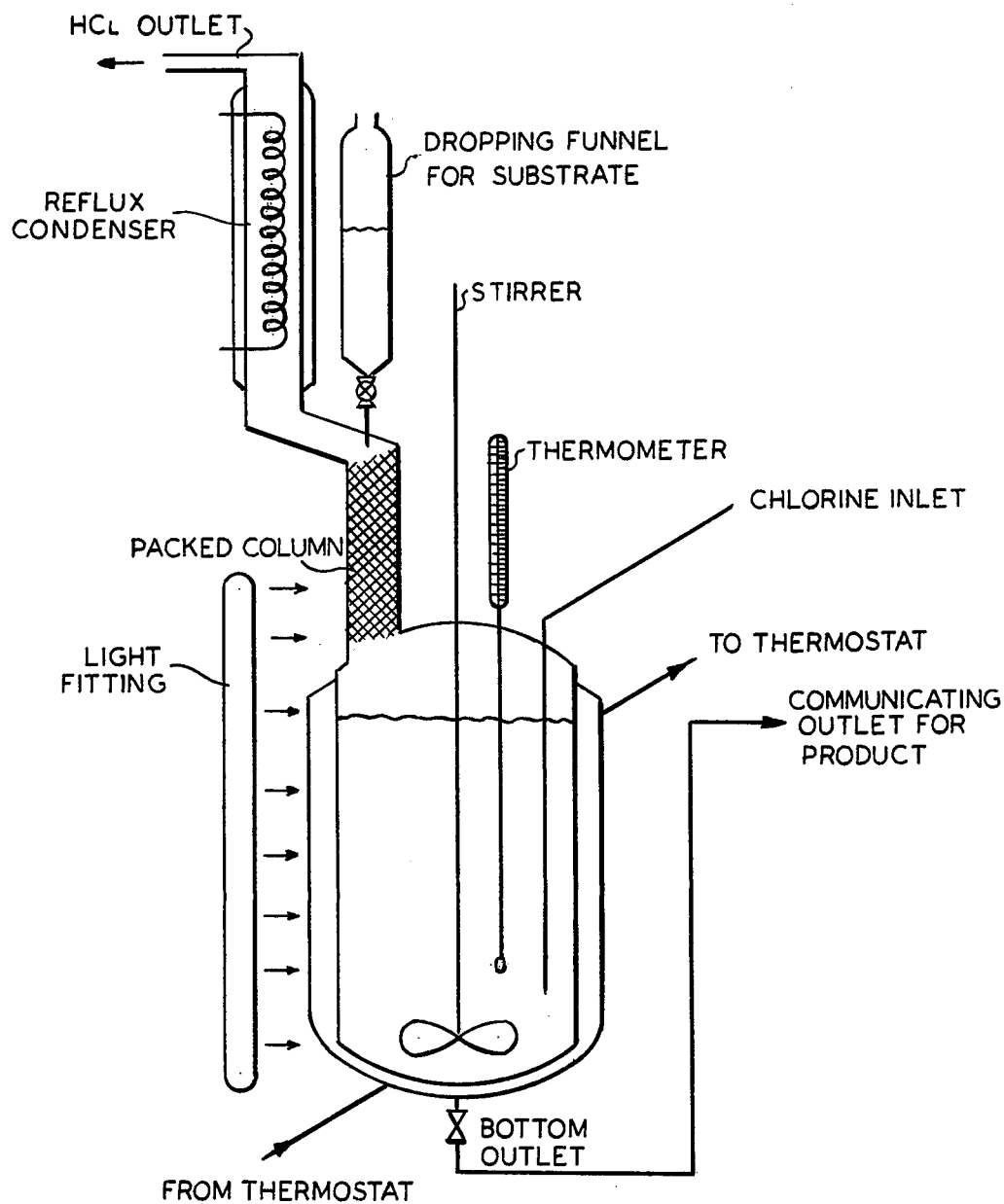

PROCESS FOR THE PREPARATION OF ALPHA-CHLOROMETHYLSILANES

BACKGROUND OF THE INVENTION

Field of the Invention

The subject of the present invention is a method for the transformation of a methyl group of methylchlorosilanes of the general formula $$(CH_3)_{4-n}SiCl_n \, (n = 0 \text{ to } 3) \qquad \text{I}$$

to a chloromethyl group for the formation of α-chloromethylsilanes of the general formula $$ClCH_2(CH_3)_{3-n}SiCl_n \qquad \text{II}$$

by chlorination with elemental chlorine during exposure to light.

DISCUSSION OF THE PRIOR ART

The α-chloromethylsilicon compounds obtainable by the present process are of considerable interest in a number of fields of application. For example, when used as adhesivizing agents for glass fiber reinforcement in resins and thermoplastics they bring about improvements in the stability of the physical properties of the materials under long-term exposure to sea water and temperature changes. Another field of application is the impregnation of inorganic pigments and fillers, such as, for example, kaolin, bentonite, chalk, iron oxides, chromium oxides, aluminum oxides, titanium dioxide, kieselgur, sand and alumina, and the improvement of adhesion in such different applications as, for example, fillers for rubber mixtures, delusterants for lacquers, in pigmentation, in cable compositions, etc. The present compounds furthermore serve as intermediates for the preparation of silanes containing functional groups in the alpha position. Despite these broad possibilities for their application, these compounds have hitherto enjoyed scarcely any economical utilization, since their production has involved great difficulty.

As it is known, the starting substances of the above General Formula I react very easily with chlorine in light, even at temperatures below ebullition, to form chlorinated products, while at the same time the system manifests a pronounced tendency towards an explosive reaction, particularly in the gaseous phase. Especially disadvantageous, however, is the high rate of multiple chlorinations which occur as a rule, and which have impaired the processes of the prior art by the considerable production of more highly chlorinated products for which no application has been found, and which have hitherto been an obstacle to the economical production of α-chloromethylsilicon compounds of the above General Formula II.

Constant attempts have therefore been made to find a method of synthesis which might provide opportunities for the economical utilization of these compounds. If, in accordance with the present state of our knowledge, a methylchlorosilane is chlorinated in the liquid phase by the introduction of chlorine with exposure to light, the yield of chloromethylsilane of Formula II is, as a rule, 60% or even less; the resulting inevitable production of unusable products of higher chlorination is always too high, even when the process is performed with a considerable reduction of the amount of chlorine.

On the basis of past knowledge, the principal causes of this difficulty have been the preferential entrance of additional chlorine into already chlorinated methyl groups and the excessive local concentration of chlorine at the point of introduction which, due to the high reactivity of the system, forms the center of the reaction. It has consequently also been proposed to distribute the chlorine uniformly into the reaction medium prior to the reaction. This is accomplished by a continuous process in which the chlorine is uniformly dissolved in the methyl silane in the dark and the reaction solution is then ignited by illumination, whereupon the system reacts violently and gaseous hydrogen chloride is liberated. In this particularly hazardous process, however, transformations higher than 5 to 6 mole-percent are prohibitive on account of the violence of the reaction, so that only low volume-time yields can be achieved. This, however, greatly limits its application on the large technical scale. Furthermore, despite the low transformation rates and the higher yields of monochlorination products of sometimes more than 80%, the reaction products still contain considerable percentages of irreducible polychlorination products.

It is an object of this invention, therefore, to provide a process for the chlorination of methylchlorosilanes whereby the chlorination proceeds such that there is obtained a monochlorination of the methyl group to be chlorinated while restricting the formation of polychlorinated products to below 5%, preferably 3%, of the total chlorination products. It is another object of this invention, therefore, to provide a commercially feasible process for the chlorination of methylsilanes to prepare monochloromethylsilanes which process can be conducted without employing hazardous conditions or increasing the risk of explosion. It is a further object of this invention to provide such a process by which the desired monochloromethylsilane compound is obtained in a yield in excess of 90 percent by weight and it is a preferred object to provide such a process which can be operated on a continuous basis over a long period of time.

SUMMARY OF THE INVENTION

In accordance with this invention, there is provided an improved process for the preparation of an α-chloromethylsilane of the general formula $$ClCH_2(CH_3)_{3-n}SiCl_n \, (n = 0 \text{ to } 3) \qquad \text{II}$$

by contacting a methylchlorosilane of the formula $$(CH_3)_{4-n}SiCl_n \qquad \text{I}$$

with elemental chlorine while exposing the reaction mixture to light, the improvement comprising introducing the elemental chlorine into a reaction zone at a constant rate, maintaining said reaction zone at a temperature in the vicinity of the boiling point of the methylsilane to be chlorinated, introducing methylsilane to be chlorinated into the reaction zone at such a rate so as to maintain the temperature of the reaction mixture in the vicinity of the boiling point of the methylsilane to be chlorinated and continuously withdrawing reaction product at such a rate that the concentration of monochloromethylsilane amounts up to 18 percent by weight. Broadly speaking, the temperature of the reaction mixture is maintained at a temperature from 5° below the boiling point of the methylsilane to be chlorinated to 12° above the boiling point of the methylsilane to be chlorinated. By such a process, yields in excess of 90% of monochloromethylsilane are provided.

In accordance with this invention, there is provided a process for the transformation of one methyl group of a methylsilane of the formula $(CH_3)_{4-n}SiCl_n$ ($n = 0$ to 3) to a chloromethyl group with the formation of an $\alpha$-chloromethylsilane of the formula $ClCH_2(CH_3)_{3-n}SiCl_n$ ($n = 0$ to 3) by chlorination with elemental chlorine with exposure of the reaction mixture to light, the process characterized in that chlorine is introduced at a constant rate into a boiling reaction mixture in a flow-through reactor containing a free outlet in the form of a communicating tube, the methylsilane to be chlorinated being introduced at such a rate that the boiling temperature of the reaction mixture remains in the vicinity of the boiling temperature of the methylsilane to be chlorinated and the reaction mixture containing the desired chloromethylsilane is continuously removed from a bottom outlet at such a rate that the concentration of the desired chloromethylsilane amounts up to 18 percent by weight.

In this continuous photochlorination in accordance with the invention, considerably improved product and volume-time yields are obtained as a result of the controlling of the monochlorination rate at up to 18 percent by sustaining the boiling temperature of the reaction mixture by metering the input of the starting substance. The substance balances of the process of the invention will result in yields of 95 to 98 percent of chloromethyl-silicon compounds with a production of only 1 to 3 percent of more highly chlorinated material, if, in a preferred method of procedure, the reaction mixture withdrawn from the bottom outlet is separated into its components and the unreacted methylchlorosilane is recycled. In view of the difficulties known from the state of the art, this surprisingly advantageous result achieved by the process of the invention could not have been expected or foreseen. The process of the invention, on account of the simplicity and safety of its performance, is capable of extension to large scale production, so that now the chloromethylsilane compounds are more economically accessible. By the process of the invention, the compounds of the above Formula II, such as, for example, chloromethyltrichlorosilane, chloromethylmethyldichlorosilane, chloromethyldimethylchlorosilane and chloromethyltrimethylsilane, are obtainable in good yield. Examples of starting substances of the above General Formula I are methyltrichlorosilane, dimethyldichlorosilane, trimethylchlorosilane and tetramethylsilane.

Chlorination is performed in a known manner by the continuous introduction of a constant amount of chlorine proportioned in gaseous form, with the irradiation of ultraviolet or visible light into the liquid reaction mixture which is being stirred and refluxed. The boiling point that establishes itself during the reaction is one which results from the boiling characteristics of all of the components of the mixture present in the liquid reaction phase, consisting substantially of chlorination product, starting silane and hydrochloric acid. It is to be insofar as possible not more than 2° to 3° above the boiling temperature of the methyl silane to be chlorinated. It can, however, also be below the boiling temperature of the methyl silane to be chlorinated, in which case, again, a tolerance of 2° to 3° is quite possible.

The boiling point that establishes itself serves as a control parameter for the proportioning of the fresh starting silane serving as raw material. If the raw material feed is reduced, the boiling temperature increases as the chlorination rate increases, on account if the constant feed of chlorine. If the raw material feed is again increased, the boiling temperature in the reactor will decrease and the chlorination rate will again fall off. Thus the reaction can be operated at quite precisely defined chlorination rates if the reaction temperature is maintained constant as described above. The boiling temperature is in general to be regulated such that the content of the chloromethyl compound in the overflow will not exceed 18 wt.-%. This is generally the case if the above-described conditions are maintained.

The process of the invention involves no special requirements as to what form of reactor is to be used. Conventional stirrer apparatus are used which are equipped internally with a temperature measuring system and a submerged gas introduction tube, and in which the substrate can be irradiated with visible or ultraviolet light. The reactor has, as shown in the diagram, on the basis of the communicating tube principle, an outlet such that the point at which its product overflows into the further processing apparatus is at the height of the liquid level which is maintained constant in the reactor. This outlet is preferably located at the bottom apex, but it can also be mounted laterally at any desired level.

Above the reactor, connected to the gaseous phase therein, is an upstanding reflux condenser from whose upper end the hydrogen chloride that forms in the chlorination reaction is carried off for reuse.

The proportioned infeeding of the starting silane takes place as a rule at the condensate return from the condenser, though it can also be located at any other desired point on the reactor. The starting silane is proportioned in liquid form, for example, through a flow meter in which the flow is regulated according to the boiling temperature desired in the reactor. The chlorine is also proportioned in gas form, for example, by means of a fixedly preset flow meter or a perforated plate ahead of the gas introduction tube. The stirring speeds are normally set at 100 to 120 revolutions per minute, but they can be considerably lower or higher, without inducing important changes in the way in which the reaction takes place in the process of the invention.

With the continuous process of the invention, volume-time yields of up to 300 g of monochlorination products per liter of reaction mixture per hour have already been obtained. Still higher throughputs are also possible, however. This fact is of especial advantage, because the production of even greater amounts can be accomplished with relatively small reactor units.

A typical reactor apparatus in the meaning of the process of the invention consists of a four-liter round flask of glass having a jacket and an internal heating coil, both of which are connected to a circulating thermostat operating as a heating unit. The flask is equipped with a conventional stirrer, such as, for example, a propeller-type, paddle-type or impeller-type stirrer. At the bottom apex of the flask is an outlet valve whose overflow is located at the liquid level desired in the flask and keeps the fill level constant. The submerged chlorine introduction tube can terminate in an open end, or it can terminate in a capillary or bubbler. Basically, the introduction of chlorine through the stirrer shaft is an entirely practical and suitable method. The irradiation is performed with visible light. Irradiation with ultraviolet light is not necessary, although it, too, will produce the reaction. For the measurement of the internal temperature the use of a thermometer having a scale calibrated in tenths of a degree is recommended. It is practical to feed the starting silane into the condensate from the reflux condenser, although the point of introduction can be selected anywhere on the reactor. In fact, a simple lateral tube injecting the silane into the tubulure at the bottom end of the condenser can be used, from which the starting silane will flow down freely into the reactor together with the descending condensate, or a mixing section constructed in the manner of a short packed column can be used, to the top of which the condensate and the proportioned starting silane is fed and sprinkles down over the ascending reaction gas. The reflux condenser is operated at low below-zero temperature, depending on the melting point of the starting silane. If for example, trimethylchlorosilane (m.p. −57° C) is used, it is advantageous to adjust the condenser to −56° C.

EXAMPLES

The process of the invention will now be explained with the aid of the following examples, which nevertheless do not restrict the scope of the invention.

EXAMPLE 1

In a four-liter flask equipped with a jacket and an internal heating coil which are connected to a circulation thermostat, and with a stirrer, a submerged gas introduction tube, a bottom outlet valve with an overflow at the level of a charge in the four-liter flask amounting to about 80% of its capacity, a reflux condenser operating at −40° C provided at its condensate outlet with a connection for the addition of the starting product, and illumination by means of a 75-Watt krypton lamp, approximately 3 liters of trimethylchlorosilane were placed and heated to gentle ebullition. A reflux temperature of 57.2° C established itself.

With the stirrer running at 110 rpm, gaseous chlorine was introduced at a rate of 20 l/h through a flow meter into the gas introduction tube, the temperature at first diminishing steadily to the turning point of 55.3° C, and then steadily increasing. When a temperature of 55.6° C was reached, the bottom outlet valve was opened, and, through a second flow meter, trimethylchlorosilane was proportioned through the inlet connection below the reflux condenser such that the boiling temperature in the reactor was maintained at 55.6° C (approx. 800 g/h).

The raw product emerging from the overflow contained 7.4% of chloromethyldimethylchlorosilane in addition to trimethylchlorosilane (the concentration of high-boiling components was below the analytic limit). The trimethylchlorosilane was continuously separated by distillation and returned entirely to the reaction flask through the second flow meter, and the chloromethyldimethylchlorosilane was purified by distillation at the boiling point of 114.8° C.

The hydrogen chloride that forms escaped in gaseous form through the reflux condenser and was taken from there without further refinement for other uses. The test for chlorine produced negative results.

After continuous operation for 104 hours at the above-described conditions, 6200 g of chloromethyldimethylchlorosilane plus 118 g of high-boiling components was obtained from 4890 g of trimethylchlorosilane. The yield of chloromethyldimethylchlorosilane thus amounted to 96.2%.

EXAMPLE 2

At the reactor operating under the same conditions as in Example 1, the continuous feeding of trimethylchlorosilane was stopped while the chlorine feed remained constant. Within a few minutes the internal temperature of the reactor rose to 56.7%. After this temperature was established, trimethylchlorosilane was again metered in, in such a manner that the reaction temperature was thereby maintained at 56.7° C. The raw product emerging from the overflow now contained 8.8% of chloromethyldimethylchlorosilane in addition to trimethylchlorosilane and 1.93% high-boiling components (with respect to the chloromethyldimethylchlorosilane)

The trimethylchlorosilane was separated by distillation and entirely recycled, and the desired product was refined by distillation. The hydrogen chloride that formed was taken for reuse as in Example 1.

After 120 hours of continuous operation under the conditions described above, 8450 g of chloromethyldimethylchlorosilane was obtained in addition to 167 g of high-boiling components, from 6670 g of trimethylchlorosilane. The yield of pure product thus amounted to 96.4%.

EXAMPLE 3

At the reactor running under the conditions of Example 2, the continuous feed of the trimethylchlorosilane was interrupted, while the chlorine feed was maintained constant. Within a few minutes the internal temperature of the reactor increased to 57.8° C. After this temperature established itself, trimethylchlorosilane was again metered in in such a manner as to maintain the reaction temperature at 57.8° C. The raw product emerging from the overflow now contained 16.5% chloromethyldimethylchlorosilane in addition to trimethylchlorosilane and 2.24% of high-boiling components (with respect to chloromethyldimethylchlorosilane). Excess trimethylchlorosilane and the hydrogen chloride produced were utilized as in the preceding examples. After 120 hours of continuous operation under the conditions described above, 15,120 g of chloromethyldimethylchlorosilane plus 387 g of high-boiling components were obtained from 12,040 g of trimethylchlorosilane. The pure product yield thus amounted to 95.4%.

EXAMPLE 4

In the apparatus described in Example 1, with the reflux condenser operating at −72° C, approximately 3 liters of tetramethylsilane were placed and heated to gentle ebullition. A reflux temperature of 26.7° C established itself.

With the stirrer operating at 110 rpm, gaseous chlorine was fed through a flow meter and through the gas introduction tube at a rate of about 20 l/h, whereupon the temperature at first dropped steadily to its turning point of 25.3° C, and then steadily rose. When a temperature of 25.7° C was reached, the bottom outlet valve was opened, and through a second flow meter, tetramethylsilane was metered in through the feed connection beneath the reflux condenser in such a manner as to maintain the boiling temperature in the reactor at 25.7° C (approximately 720 g/h).

The raw product emerging from the overflow contained 8.2% of chloromethyltrimethylsilane in addition to tetramethylsilane (the concentration of high-boiling components was below the analytic limit). The tetramethylsilane, after distillative separation, was returned entirely to the reaction flask and the chloromethyltrimethylsilane was refined by distillation at the boiling point of 97.1° C.

The hydrogen chloride that was produced was utilized without refinement. The test for chlorine had a negative result.

After 192 hours of continuous operation under the conditions described above, 11320 g of chloromethyltrimethylsilane plus 142 g of high-boiling components was obtained from 8380 g of tetramethylsilane. The chloromethyltrimethylsilane yield thus amounted to 97.1%.

EXAMPLE 5

At the reactor running under the conditions of Example 4, the continuous feed of tetramethylsilane was stopped while the chlorine feed was maintained constant. Within a few minutes the internal temperature of the reactor rose to 26.9° C. After this temperature was established, tetramethylsilane was again metered in such that the reaction temperature was maintained at 26.9° C. The raw product emerging from the overflow now contained 13.9% of chloromethyltrimethylsilane plus tetramethylsilane and 2.0% of high-boiling components (with respect to chloromethyltrimethylsilane).

After 72 hours of continuous operation under the conditions described above, 10,200 g of chloromethyltrimethylsilane was obtained plus 266 g of high-boiling components, from 7490 g of tetramethylsilane. The pure product yield was thus 97.0%.

EXAMPLE 6

At the reactor operating under the conditions of Example 5, the continuous feeding of tetramethylsilane was interrupted, while the feeding of chlorine was maintained constant. Within a few minutes the internal temperature of the reactor rose to 28.0° C. After this temperature was reached the tetramethylsilane was again metered in, in such a manner that the reaction temperature was maintained at 28.0° C. The raw product emerging from the overflow now contained 18.4% of chloromethyltrimethylsilane plus tetramethylsilane and 3.8% of higher-boiling components (with respect to chloromethyltrimethylsilane).

After 120 hours of continuous operation under the conditions described above, 15,900 g of chloromethyltrimethylsilane plus 605 g of high-boiling components were obtained from 12,020 g of tetramethylsilane. The pure product yield thus amounted to 95.0%.

EXAMPLE 7

In the apparatus described in Example 1, with the reflux condenser operating at −72° C, approximately 3 liters of methyltrichlorosilane was placed and heated to gentle ebullition. A reflux temperature of 66.1° C established itself.

With the stirrer operating at 120 rpm, gaseous chlorine was introduced through a flow meter and the gas introduction tube at a rate of about 20 l/h, the temperature first steadily diminishing to its turning point of 64.7° C, and then steadily rising. When a temperature of 65.3° C was reached, the bottom outlet valve was opened, and through a second flow meter methyltrichlorosilane was metered in through the inlet connection under the reflux condenser so as to maintain the boiling temperature in the reactor at 65.3° C.

The raw product emerging from the overflow contained 7.1% of chloromethyltrichlorosilane plus methyltrichlorosilane (the concentration of higher-boiling components was below the analytic limit). The methyl trichlorosilane was separated by distillation and recycled entirely and the chloromethyltrichlorosilane was refined by distillation at the boiling point of 116.2° C.

The hydrogen chloride produced was utilized without refinement. The test for chlorine was negative.

After 193 hours of continuous operation under the above-described conditions, 12,670 g of chloromethyltrichlorosilane plus 212 g of higher-boiling components were obtained from 10,660 g of methyltrichlorosilane. The yield of chloromethyltrichlorosilane thus amounted to 96.7%.

EXAMPLE 8

At the reactor running under the conditions of Example 7, the continuous feeding of methyltrichlorosilane was stopped while the feeding of chlorine was maintained constant. In a few minutes the internal temperature of the reactor increased to 66.3° C. After this temperature established itself, the methyltrichlorosilane was again metered in at such a rate as to maintain the reaction temperature at 66.3° C. The raw product emerging from the overflow now contained 10.7% of chloromethyltrichlorosilane plus methyltrichlorosilane and 2.5% of higher-boiling components (with respect to chloromethyltrichlorosilane).

After 80 hours of continuous operation under the conditions described above, 7,780 g of chloromethyltrichlorosilane plus 227 g of higher-boiling components was obtained from 6,630 g of methyltrichlorosilane. The total yield of pure product was thus 95.4%.

EXAMPLE 9

At the reactor operating under the conditions of Example 8, the continuous feeding of methyltriclorosilane was stopped, while the feeding of chlorine was continued at a constant rate. Within a few minutes the internal temperature of the reactor increased to 67.1° C. After this temperature was established, methyltrichlorosilane was again metered in in such a manner as to maintain the reaction temperature at 67.1° C. The raw product emerging from the overflow now contained 16.8% chloromethyltrichlorosilane plus methyltrichlorosilane and 3.8% higher-boiling components (with respect to chloromethyltrichlorosilane).

After 72 hours of continuous operation under the above-described conditions, 11,020 g of chloromethyltrichlorosilane plus 462 g of higher-boiling components were obtained from 9510 g of methyltrichlorosilane. The total yield of the pure product thus amounted to 94.2%.

EXAMPLE 10

In the apparatus described in Example 1, with the reflux condenser operating at −72° C, approximately 3 liters of dimethyldichlorosilane were placed and heated to gentle ebullition. A reflux temperature of 70.0° C established itself.

With the stirrer running at 120 rpm, gaseous chlorine was introduced through a flow meter and the gas introduction tube at a rate of about 20 l/h, whereupon the temperature at first diminished steadily to its turning point at 68.7° C, and then steadily rose. When a temperature of 69.4° C was reached the bottom outlet valve was opened and through a second flow meter, dimethyldichlorosilane was metered into the feed connection beneath the reflux condenser so as to maintain the boiling temperature in the reactor at 69.4° C.

The raw product emerging from the overflow contained 7.5% of chloromethylmethyldichlorosilane (the concentration of any higher-boiling components was below the analytic limit). The dimethyldichlorosilane, after separation by distillation, was entirely recycled, and the chloromethylmethyldichlorosilane was rectified at the boiling point of 121.2° C.

The hydrogen chloride produced was utilized without refinement. The test for chlorine was negative.

After 72 hours of continuous operation under the conditions described above, 4650 g of chloromethylmethyldichlorosilane was obtained plus 37 g of higher-boiling components. The chloromethylmethyldichlorosilane thus amounted to 96.7%.

EXAMPLE 11

At the reactor operating under the conditions of Example 10, the continuous feeding of dimethyldichlorosilane was stopped, while the feeding of chlorine was maintained constant. Within a few minutes the internal temperature of the reactor rose to 70.6° C. After this temperature was established, dimethylchlorosilane was again metered in, at such a rate that the reaction temperature was maintained at 70.6° C. The raw product emerging from the overflow now contained 11.9% of chloromethylmethyldichlorosilane plus dimethyldichlorosilane and 2.3% of higher-boiling components (with respect to chloromethymethyldichlorosilane).

After 72 hours of continuous operation under the above-described conditions, 7360 g of chloromethyldichlorosilane plus 202 g of higher-boiling components were obtained from 6050 g of dimethyldichlorosilane. The total yield of pure product thus amounted to 96.0%.

What is claimed is:

1. In a process for the preparation of an α-chloromethylsilane of the general formula $$ClCH_2(CH_3)_{3-n}SiCl_n \ (n = 0 \text{ to } 3) \qquad II$$

by contacting a methylsilane of the formula $$(CH_3)_{4-n}SiCl_n \qquad I$$

with elemental chlorine under illumination, the improvement which comprises introducing chlorine into a reaction zone at a constant rate, maintaining said reaction zone in the vicinity of the boiling point of the methylsilane to be chlorinated, introducing methylsilane to be chlorinated into said reaction zone at such a rate so as to maintain the temperature of the reaction mixture in the vicinity of the boiling point of the methylsilane to be chlorinated and continuously withdrawing reaction product at such a rate that the concentration of chloromethylsilane in the reaction product amounts to up to 18 percent by weight.

2. A process according to claim 1 wherein the methylsilane to be chlorinated is introduced into the reaction mixture at such a rate so as to maintain the temperature of the reaction mixture at a temperature from 5° below the boiling point of the methylsilane to 12° above the boiling point of the methylsilane.

3. A process according to claim 2 wherein unreacted methylsilane is separated from the reaction product and recycled to the reaction zone.

4. A process according to claim 2 wherein the temperature of the reaction zone is maintained from 3° below the boiling point of the methylsilane to be chlorinated to 3° above the boiling point of the methylsilane to be chlorinated.

5. A process according to claim 1 wherein the components of the reaction mixture are refluxed.

6. A process according to claim 1 wherein the methylsilane is methyltrichlorosilane, dimethyldichlorosilane, trimethylchlorosilane or tetramethylsilane.

7. A process according to claim 1 wherein the reaction zone is a generally vertical reaction zone equipped with a reflux condenser in the vapor space above the reaction zone and gaseous chlorine is introduced into the reaction zone and permitted to flow vertically upwardly through liquid components of the reaction mixture.

8. A process according to claim 7 wherein the reaction zone is equipped with a stirrer, the reaction mixture is stirred and chlorine is introduced into the reaction mixture by passing the same through a hollow shaft of the stirrer and admitting the same into the reaction mixture from the bottom of the stirrer element.

9. A process according to claim 5 wherein the reaction mixture is refluxed employing a reflux condenser operated at a sub-0° temperature and above the melting point of the methylsilane to be chlorinated.

* * * * *